US010302608B1

(12) United States Patent
Robinson, Jr. et al.

(10) Patent No.: US 10,302,608 B1
(45) Date of Patent: *May 28, 2019

(54) MONOLITH CATALYST TEST SYSTEM AND METHOD FOR ITS USE

(71) Applicant: Catalytic Combustion Corporation, Bloomer, WI (US)

(72) Inventors: John W. Robinson, Jr., Bloomer, WI (US); Don R. Verdegan, Bloomer, WI (US); Mike J. Werner, Bloomer, WI (US); Mark Sokolowski, Bruce, WI (US)

(73) Assignee: Catalytic Combustion Corporation, Bloomer, WI (US)

( * ) Notice: Subject to any disclaimer, the term of this patent is extended or adjusted under 35 U.S.C. 154(b) by 79 days.

This patent is subject to a terminal disclaimer.

(21) Appl. No.: 15/425,721

(22) Filed: Feb. 6, 2017

Related U.S. Application Data (63) Continuation of application No. 14/753,425, filed on Jun. 29, 2015, now Pat. No. 9,562,880, which is a continuation-in-part of application No. 13/432,408, filed on Mar. 28, 2012, now Pat. No. 9,068,954.

(51) Int. Cl.
| | | |
|---|---|---|
| *G01N 31/10* | (2006.01) | |
| *B01J 35/04* | (2006.01) | |
| *F01N 11/00* | (2006.01) | |
| *B01D 53/94* | (2006.01) | |

(52) U.S. Cl.
CPC ............. *G01N 31/10* (2013.01); *B01J 35/04* (2013.01); *F01N 11/00* (2013.01); *B01D 53/94* (2013.01); *F01N 2550/02* (2013.01)

(58) Field of Classification Search
CPC ...................................................... G01N 31/10
USPC .......................... 436/37, 155, 159–160, 181
See application file for complete search history.

(56) References Cited

U.S. PATENT DOCUMENTS

| | | | |
|---|---|---|---|
| 3,431,077 | A | 3/1969 | Danforth |
| 3,536,452 | A | 10/1970 | Norton et al. |
| 3,583,230 | A | 6/1971 | Patterson |
| 4,099,923 | A | 7/1978 | Milberger |
| 4,221,568 | A | 9/1980 | Boettger |
| 5,959,297 | A | 9/1999 | Weinberg et al. |
| 6,063,633 | A | 5/2000 | Willson, III |
| 6,238,929 | B1 | 5/2001 | Antonenko et al. |
| 6,333,196 | B1 | 12/2001 | Willson, III |
| 6,426,226 | B1 | 7/2002 | Senkan |
| 6,576,470 | B1 | 6/2003 | Windhab et al. |
| 6,627,257 | B1 | 9/2003 | Foerster et al. |
| 6,864,091 | B1 | 3/2005 | Wang et al. |
| 7,052,914 | B2 | 5/2006 | Maier et al. |
| 7,435,598 | B2 | 10/2008 | Vaughn et al. |
| 7,635,593 | B2 | 12/2009 | Muzio et al. |
| 8,273,185 | B2 | 9/2012 | Milles et al. |
| 8,418,684 | B2 | 4/2013 | Robinson, Jr. |

(Continued)

*Primary Examiner* — Arlen Soderquist
(74) *Attorney, Agent, or Firm* — Gable Gotwals (57) ABSTRACT

A system and method for non-destructive testing of a monolith catalyst element includes a a piping arrangement located above and below the element that seals against a portion of the element. A test fluid passes between the piping and therefore through the portion of the sealed catalyst section. Ports located in the piping allow for sampling of the fluid before and after the catalyst section. The catalyst element may then be repositioned for testing of a second portion of the element.

27 Claims, 10 Drawing Sheets

(56) References Cited

U.S. PATENT DOCUMENTS

| | | |
|---|---|---|
| 9,068,954 B1 | 6/2015 | Robinson, Jr. et al. |
| 9,341,545 B2 * | 5/2016 | Forster .................... F01N 11/00 |
| 9,562,880 B1 * | 2/2017 | Robinson, Jr. ......... G01N 31/10 |
| 2002/0182128 A1 | 12/2002 | Carnahan et al. |
| 2004/0261379 A1 * | 12/2004 | Bruun .................... F23C 13/00 |
| | | 55/418 |
| 2005/0050950 A1 * | 3/2005 | Anderson ............. F23D 11/103 |
| | | 73/114.77 |
| 2006/0246593 A1 | 11/2006 | Towler |
| 2008/0178413 A1 | 7/2008 | Wagner et al. |
| 2008/0295690 A1 | 12/2008 | Ehlers |
| 2009/0056288 A1 | 3/2009 | Waldo |
| 2009/0238751 A1 | 9/2009 | Wilhite et al. |
| 2012/0111370 A1 | 5/2012 | Milles et al. |

\* cited by examiner

MONOLITH CATALYST TEST SYSTEM AND METHOD FOR ITS USE

CROSS REFERENCE TO PENDING APPLICATIONS

This application is a continuation application which claims priority to U.S. patent application Ser. No. 14/753,425, filed Jun. 29, 2015, which was a continuation-in-part application which claims priority to U.S. patent application Ser. No. 13/432,408, filed Mar. 28, 2012, U.S. Pat. No. 9,068,954, which are incorporated herein by reference.

BACKGROUND OF THE INVENTION

This invention relates generally to systems, apparatuses, and methods useful in testing the performance of a monolith catalyst. More specifically, this invention relates to systems, apparatuses, and methods for non-destructive testing of a monolith catalyst like those used in industrial engine emission control. Notwithstanding the above, the underlying principles could be used for testing any large monolith catalyst element.

There are two methods for testing the activity of a monolith catalyst. The first method removes a small portion of the catalyst element, places that portion or sample core into a small test system, and uses synthetic gas mixtures to test the core and determine the overall activity of the catalyst. For example, catalysts used in industrial engines have outside dimensions from about 6 to 40 inches across and the removed core can be about 1 inch diameter. The second method tests the entire catalyst element by installing the element into a system that passes either engine exhaust or a synthetic gas mixture over the element.

The first method, sampling, has two major disadvantages: sampling error and catalyst damage or failure. Sampling error comes about because the activity of the catalyst element can vary across its face. Therefore, the sample core may test at higher or lower activity than the element as a whole and introduce significant sampling error into the test results. Catalyst failure comes about in a couple of ways. First, because reinstalling the core into the element is challenging, the hole created by the removed sample core is often plugged to prevent flow passing through it. This reduces the available catalyst volume and detriments the performance of the catalyst element as a whole. Additionally, any leakage around the plug or reinstalled core impairs performance. Fear of damaging the element leads people to test a limited amount of it—and thereby increase sampling error—because every core removed presents another opportunity to damage the overall element. Second, the process of removing the core can cause loss of coating material in the core itself. This not only detriments the analysis but because some catalyst elements have layers of metal foil that are not bound together, the element can either fall apart or destroy its cellular structure. Roughly half of all industrial engine monolith catalyst manufacturers do not affix layers and cutting operations can shake off about half of the coating.

The second method, whole element testing, eliminates sampling error and catalyst failure, but it too has a couple of problems. First, the method is resource and cost intensive because an engine has to be used to generate the test gas or a synthetic gas mixture must be used. If a synthetic gas mixture is used, tanks must be purchased to supply the gas and the entire gas stream must be heated above 700° F. If an engine is used, it must be fueled and maintained. And the engine also introduces error to the testing because a wide range of factors affect engine exhaust, factors such as engine wear, ambient conditions, fuel quality, and oil quality. Second, the quality of data obtained from the test depends upon having the correct "space velocity," that is, the correct ratio between the flow rate of gas through the catalyst and the volume of catalyst material. Because of the wide range of catalyst sizes and shapes employed by the various catalyst suppliers, the tester must have right equipment, jigs and fixtures to hold each size and shape in the gas flow. This leads to having a lot of equipment on-hand and the time consuming changeover that results. Additionally, the tester must produce sufficient gas flow for the specific catalyst either by using a series of engines or supplying a large amount of synthetic gas.

In summary, the first method, sampling, introduces significant sampling error and destroys a portion of the catalyst element. The second method, whole element testing, is very inefficient and difficult to set up given the wide range of sizes and shapes of catalyst elements employed by the industry.

SUMMARY OF THE INVENTION

A monolith test system made according to this invention allows efficient, non-destructive activity testing of monolithic catalyst elements. The system allows the activity of a small section of the overall catalyst element to be tested without removing it from the element. This is accomplished by directing a gas through pipes having means of sealing them against the surface of the catalyst being tested. In principle, any temperature, gas flow rate, and pipe diameter can be used. Multiple runs are conducted at different regions of the element's face in order to assess the activity level of the whole. The gas composition could also be varied to allow testing of any catalyst system.

Objects of this invention include providing an activity test system for monolithic catalysts that does not damage the catalyst, allows adequate samples to be tested in an efficient manner, and does not require different jigs and fixtures to accommodate different sized and shaped catalysts.

ELEMENTS AND NUMBERINGS USED IN THE DRAWINGS AND DETAILED DESCRIPTION

10 Test system
20 Test stand
21 Table-top, flat surface
31 Blower (source of main fluid)
33 Blower outlet piping
35 Heater
37 Heater outlet piping
41 Propane cylinder (source of test fluid)
43 Propane piping
50 Catalyst inlet pipe
51 Opening
52 Flange
53 Gasket or sealing end (sealing means)
54 Table-top surface opening
55 Upper end
59 Port
60 Catalyst outlet pipe
61 Flange
63 Gasket or sealing end (sealing means)
65 Pipe expansion joint
66 Lower end
67 Screw jack (raising and lowering means)
69 Port
70 Pivot table
74 Pivot table-top surface opening
77 Slides
79 Stop
80 Catalyst inlet pipe adaptor
83 Gasket or sealing end (sealing means)
85 Upper end
89 Lower end
90 Catalyst outlet pipe
93 Gasket or sealing end (sealing means)
97 Screw jack (axial or linear adjustment means)

DETAILED DESCRIPTION OF THE PREFERRED EMBODIMENTS

A test system 10 made according to this invention allows a section of a monolithic catalyst element to be tested without requiring a piece of the catalyst to be removed from the element. Although the system 10 described herein is intended for use catalyst elements typically found in industrial engines, the system 10 could be used to test any monolithic catalyst element for any industry. These elements are especially common in a range of environmental compliance process units.

Referring to FIGS. 1 to 5, testing is accomplished by providing a means of conveying fluid through the catalyst element and allowing those means to test different areas or sections of the element. A preferred embodiment uses a test stand 20 which includes piping above and below the catalyst as the conveying means, air as the main fluid and propane as the test fluid, that is, the constituent fluid acted upon by the catalyst element. A blower 31 creates the air stream and passes it into a blower outlet piping 33 which is connected to a heater 35. The heater 35 heats the blown air stream to a desired test temperature. The heated air stream then passes into a heater outlet piping 37. A propane cylinder 41 introduces a propane stream into a propane piping 43 which bypasses heater 35. Downstream of the heater 35, the heated air stream and the propane stream meet and pass through a static mixer (not shown) located in a catalyst inlet pipe 50 and become thoroughly mixed together ("the mixed stream").

Note that compounds other than propane may be used as the test fluid. Propane was selected as the test fluid here because of its standard commercial composition across the country, local availability, general familiarity with its storage and use due to its widespread use as a cooking fuel for barbeque grills, the odorant that is incorporated in it as an indicator of leakage, its low cost compared to other potential test compounds and the fact that it is often found in the normal constituents of the exhaust from industrial engines. However, any compound that is gaseous at the desired test temperature and capable of being acted upon by the catalyst element can be used as the test fluid.

Figure 1:
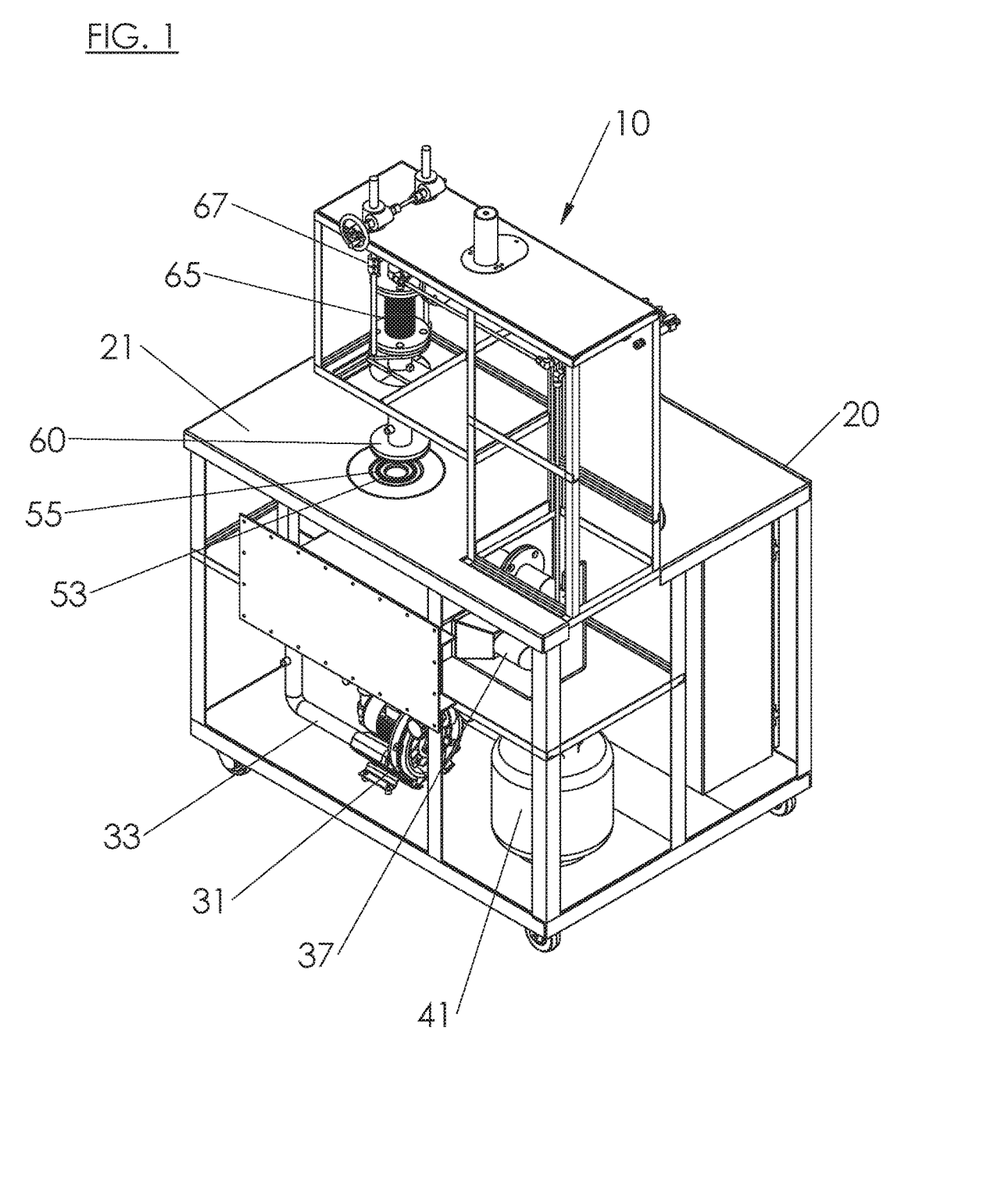
FIG. 1 is an isometric view of a preferred embodiment of a test stand which practices the system and method of this invention. Various panels have been removed from the stand in order to present the stand's contents. A catalyst element to be tested is placed on the stand's table top and a section of the element is sealed between a catalyst inlet pipe which delivers a test fluid and a catalyst outlet pipe which receives the test fluid after it has passed through the section. The stand allows various sections of the catalyst to be tested.

The mixed stream of propane and heated air then proceeds to an opening 51 at the upper end of catalyst inlet pipe 50. The opening 51 is flush with a large, table-top, flat surface 21 of the test stand 20 which supports the catalyst element. A gasket 53 located at the upper end 55 of the catalyst inlet pipe 55 provides sealing means against the lower or inlet face of the catalyst section being tested. The test stand 20 may be provided with means to adjust the height of the opening 51 relative to the flat surface 21 to ease the movement of the catalyst element across the flat surface 21 without damaging the gasket 53. A thermocouple (not shown) placed at the inlet face of the catalyst section controls the temperature of the mixed stream. Preferably, the thermocouple is installed with its tip flush with the upper end 55 of the catalyst inlet pipe 50 to control the temperature of the mixed stream.

The mixed stream of propane and heated air then proceeds to an opening 51 at the upper end of catalyst inlet pipe 50. The opening 51 is surrounded by a flange 52 that is flush with a large, table-top, flat surface 21 of the test stand 20 which supports the catalyst element. There is an opening 54 in the table-top surface surrounding the upper end of the catalyst inlet pipe. A gasket 53 located at the upper end 55 of the catalyst inlet pipe 50 provides sealing means against the lower or inlet face of the catalyst section being tested. The test stand 20 may be provided with means to adjust the height of the opening 51 relative to the flat surface 21 to ease the movement of the catalyst element across the flat surface 21 without damaging the gasket 53. A thermocouple (not shown) placed at the inlet face of the catalyst section controls the temperature of the mixed stream. Preferably, the thermocouple is installed with its tip flush with the upper end 55 of the catalyst inlet pipe 50 to control the temperature of the mixed stream.

The mixed stream exits opening 51 and flows into and through the catalyst section. A flow meter (not shown) allows measurement and control of the mixed stream flow through the catalyst section. Due to the structured nature of monolithic catalysts, the mixed stream flow is restricted radially to the diameter of the opening 51. A catalyst outlet pipe 60 is provided on the upper or outlet face of the catalyst element. The outlet pipe 60 is essentially identical to the catalyst inlet pipe 50, has the same diameter opening as that of opening 51, and is aligned concentrically relative to the inlet pipe 50. A gasket 63 located in a flange 61 surrounding the opening provides sealing means against the outlet face of the catalyst section being tested. A thermocouple (not shown) is installed with the tip flush with the opening of the outlet pipe to allow measurement of the mixed stream at the outlet side of the catalyst section. The mixed stream then passes through the outlet pipe 60 and is exhausted.

Figure 2:
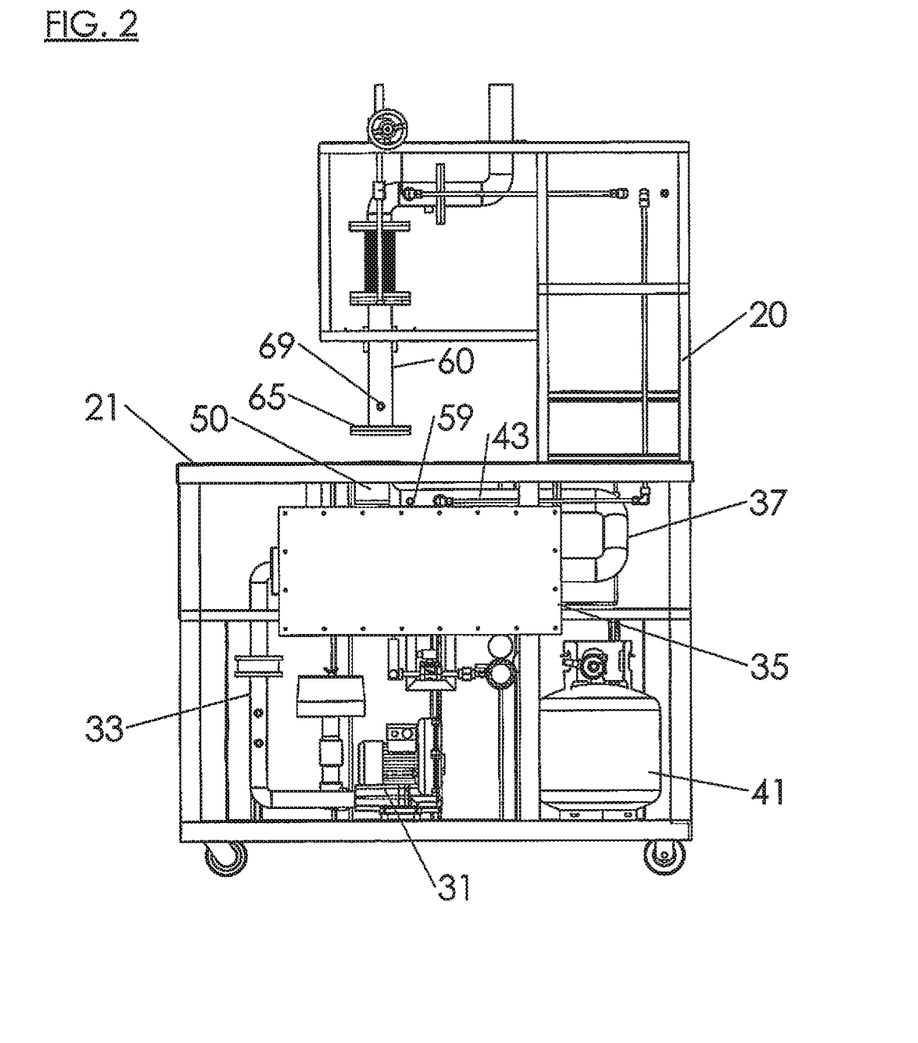
FIG. 2 is an front elevation view of the test stand of a FIG. 1. A blower supplies a main fluid stream which is passed through a heater to heat it to the desired temperature. A propane cylinder supplies a test fluid which bypasses the heater and mixes with the heated main fluid stream. The catalyst outlet pipe is vertically displaceable relative to the table top.

Either the flat surface 21 or the catalyst outlet pipe 60 must be provided with means to raise or lower it and allow the catalyst element to be installed and removed from the test stand 20. In a preferred embodiment, the catalyst outlet pipe 60 is raised and lowered. The raising and lowering means is a pipe expansion joint 65 installed in the length of the outlet pipe 60 and a screw jack 67 is used to raise and lower the outlet pipe. Other raising and lowering means could be used.

Figure 5:
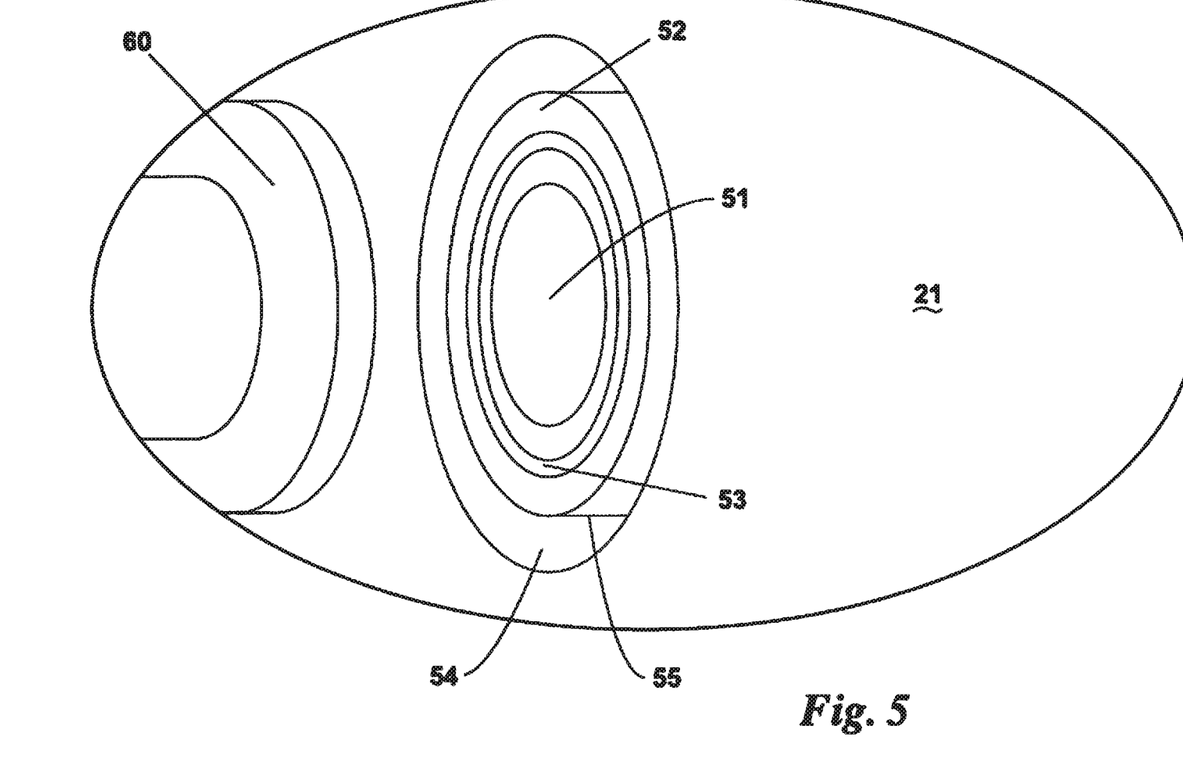
FIG. 5 is an enlarged view of a section of the system of FIG. 1 surrounding the catalyst inlet pipe and the catalyst outlet pipe arranged to test catalyst elements in a vertical orientation.

This system provides a method for sealing a pipe or tube to the inlet and outlet faces of the catalyst. This allows different sections of the catalyst to be tested without removing a piece of the catalyst. For example, on a 32-inch diameter catalyst element, 6 to 8, 2-inch sections can be tested. On a 12-inch diameter catalyst element, 3 2-inch sections can be tested. The minimum, maximum and average performance can then be calculated. The invention also allows one or both sealing surfaces to be moved in a vertical direction to allow testing of a range of catalyst thicknesses. Although the example illustrated in FIGS. 1-4 shows the catalyst element in a horizontal orientation with the catalyst inlet and outlet pipes 50, 60 arranged vertically in relation to the catalyst, test stand 20 could be configured with the catalyst inlet and outlet pipes 50, 60 arranged to test catalyst elements in a vertical orientation as shown in FIG. 5 (or some other angular orientation). An essential feature of the invention is aligning the catalyst inlet and outlet pipes 50, 60 with each other and placing the pipes 50, 60 in sealing relationship to the catalyst element in order to test any section of that element without having to remove a portion of it or install a separate reactor.

Regardless of the orientation of the catalyst element, ensuring good sealing is key to getting consistent results when performing catalyst tests. The traditional way of accomplishing good sealing, and the way used in the test methods discussed in the Background section, is to install the catalyst into a piping system sealed with typical piping methods. Test system 10 employs a different approach, namely, clamping a section the catalyst element between two flexible piping structures 50, 60 having appropriate sealing means 53, 63. This different approach allows the purposes of this invention to be accomplished.

Figure 3:
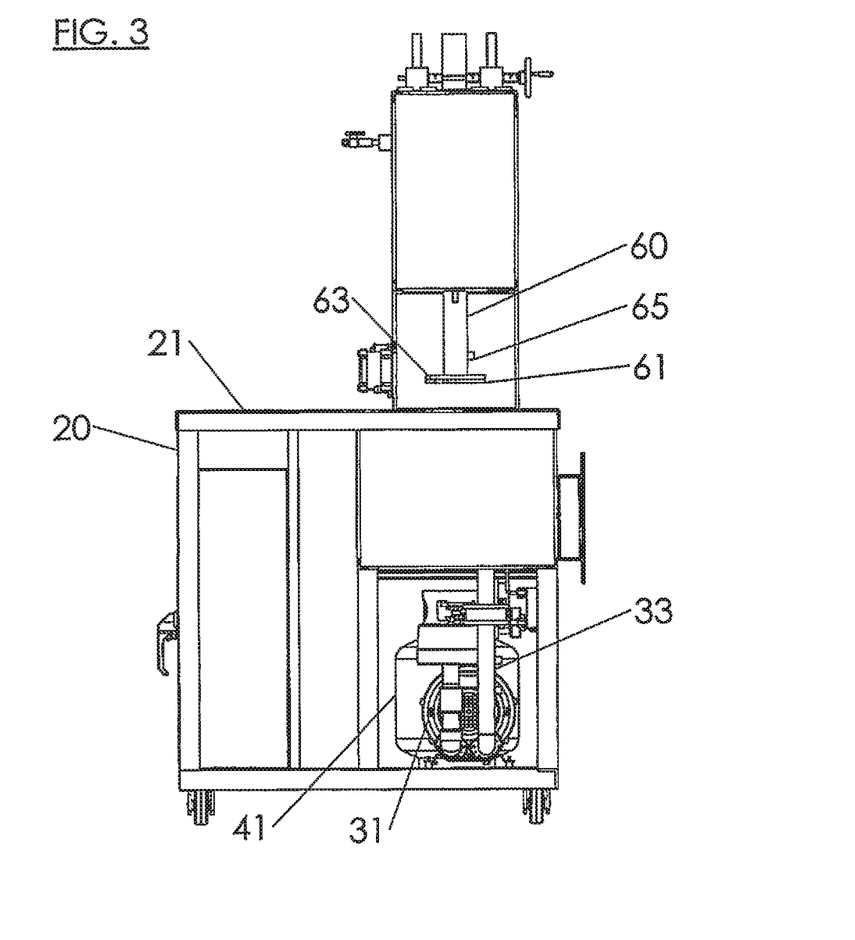
FIG. 3 is a left side elevation view of the test stand of FIG. 1. A port located on the catalyst outlet pipe allows for sampling of the fluid stream after it has passed through the section being tested. A similar port is located on the catalyst inlet pipe.
Figure 4:
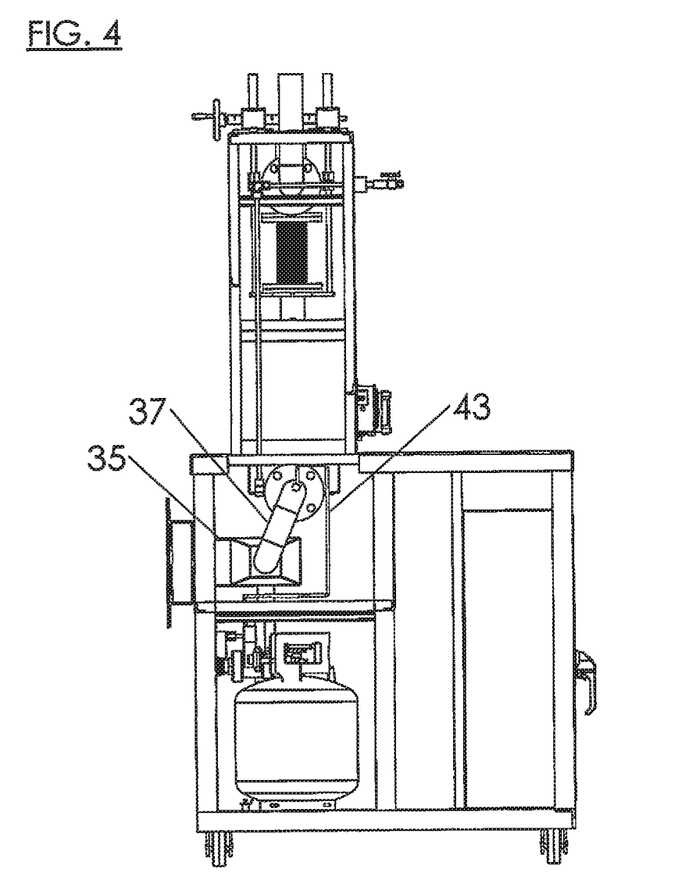
FIG. 4 is a right side elevation view of the test stand of FIG. 1.

To determine the activity of the catalyst at the section of the element tested, one or more compounds or species of the mixed stream must be expected to be affected by the catalyst at the test temperature. The mixed stream is sampled with the use of two ports 59, 69 in the inlet pipe 50 upstream of the catalyst and the outlet pipe 60 downstream of the catalyst, respectively. This allows the concentration of the species of interest to be determined before and after the catalyst. The concentrations can then be used to determine a conversion across the catalyst.

The concentrations can be measured through the use of an analytical instrument that is capable of detecting the compound(s) being introduced to the catalyst. A listing of such instruments includes but is not limited to portable gas measuring equipment for monitoring engine exhaust, flame ionization detector, and gas chromatograph. The type of analytical instrument used is not critical to the operation of the test system 10 as any of these instruments can provide the information needed to assess the performance of the catalyst being evaluated. The operator makes the choice of instrumentation based on the cost to purchase and the complexity of operation for the instrument against the degree of sensitivity and resolution they desire in the data obtained.

The preferred embodiments disclosed herein are the result of a number of design iterations. The original test system was built with a smaller primary heater and included a heat exchanger. The gas flowed through the heat exchanger, through the heater, through the catalyst, and then through the heat exchanger again. The purpose of the heat exchanger was to recover heat from the outlet gas stream and use it to preheat the inlet gas in order to reduce energy demands. This design took up more space and did not reliably achieve the desired reaction temperature at the desired flow rate.

A second iteration involved removing the heat exchanger and adding a second heater in series with the first heater (i.e., the gas flowed over one heater and then over the second). This configuration allowed the desired temperature to be achieved at the desired flow rate, but the heaters failed after an unacceptably short period of operation.

A third iteration placed the two heaters in parallel (i.e., the gas flow was distributed over both heaters simultaneously). This configuration did not allow the desired temperature to be achieved, so a third heater was placed upstream of the other two. The gas flowed over the single heater and then was distributed over the other two heaters. This three-heater layout allowed the reaction temperature to be achieved at the desired flow rate with a reasonable heater life.

After appropriate flow rates and temperatures were achieved, the test gas injection system was tested. Initially, it appeared the injection system was working as expected, but then inconsistencies began to appear as the testing progressed because the test gas was not fully mixed in the bulk gas stream. The uneven distribution of gas led to a radial concentration gradient in the pipes and across the catalyst and caused inconsistent results. At the time, the test gas was conveyed through a ¼-inch tube which was connected to the wall of the test stand pipe. The gas appeared to be staying against the pipe wall instead of dispersing into the entire stream.

To correct the uneven distribution of test gas, a series of nozzles that directed the test gas flow into the center of the pipe were prepared and tested. The nozzles failed to correct the distribution problem on their own. A nozzle was left on the test gas system, and a static mixing device was added downstream from the test gas injection point. This finally led to good mixing of the test gas into the bulk stream.

As testing continued, the flat surface or table top that the catalyst is placed on for the tests warped and prevented proper sealing of the flanges at the catalyst face. To correct this, a new table top was designed. The new table top 21 used a different grade of stainless steel (preferably, for example, AISI type 304 or 409) having a smaller coefficient of thermal expansion. Thicker steel was used to help control the warping. A larger circle was also cut around the heated (catalyst inlet) pipe 50. The larger opening 54 lowered the temperature gradient to which the steel was exposed. These three changes led to a significant reduction in the warping that was taking place and allowed the flanges to consistently seal against the face of the catalyst section being tested.

The final phase of testing involved establishing appropriate test conditions. The goal of this testing was to determine the change in activity of a catalyst after a catalyst cleaning procedure. Test conditions (specifically, flow rate and temperature) needed to be selected to allow changes in catalyst performance to be detected. If the temperature was too high or the flow rate too low, most catalysts would achieve complete or nearly complete conversion of the test gas, and it would not be possible to distinguish active and inactive catalysts. If the test temperature was too low or the flow rate was too high, even active catalyst would not perform well and all the catalysts would cluster tightly near zero conversion. Routine experimentation of the kind typically done in the art led to a range of temperatures and flow rates that allowed the activity before and after the cleaning process to be differentiated.

A test system 10 made according to this invention has immediate practicality in the area of industrial engine exhaust emissions. The system 10 allows an engine catalyst to be tested in order to determine the extent of deactivation the catalyst has undergone during use. The catalyst can be cleaned and retested to determine if it still has useful life remaining or if it has been deactivated beyond recovery. Because the cleaning process is significantly more cost effective than purchasing a new catalyst, engine operators have been willing to have it done when using the prior art test methods but risk extended downtime by reinstalling a cleaned but deactivated catalyst. The cleaned, deactivated catalyst would fail emissions testing and the operator would have to uninstall and replace the catalyst. Additionally, beyond the labor costs incurred by reinstalling a deactivated catalyst, the operator risks exposure to fines and penalties from EPA and respective state agencies because the engine's emissions are no longer in compliance with operating permits. Having an efficient testing procedure like that provided by system 10 allows the catalyst to be cleaned and tested for less than the cost of a new catalyst element while providing operators a method of determining the activity of the catalyst prior to its reinstallation.

The test system 10 also provides a non-destructive method of efficiently testing monolithic catalyst elements. As discussed in the Background section, existing methods require removing part of the element for testing or installing the entire element into a test system. This risks leakage or catalyst failure in the first case or, in the second case, is too expensive to be used.

Referring now to FIGS. 6 to 10, an alternate embodiment of a test system 10 made according to this invention allows a section of a monolithic catalyst element to be tested without the element being removed from its housing "H". Testing occurs in the same manner as previously described but additional structure is used to convert test stand 20 into one that can accommodate a housed catalyst element. The additional structure includes a pivot table 70 with adjustable slides 77 and a catalyst inlet pipe adaptor 80 that connects to the inlet pipe 50 and blocks outlet pipe 60.

Figure 7:
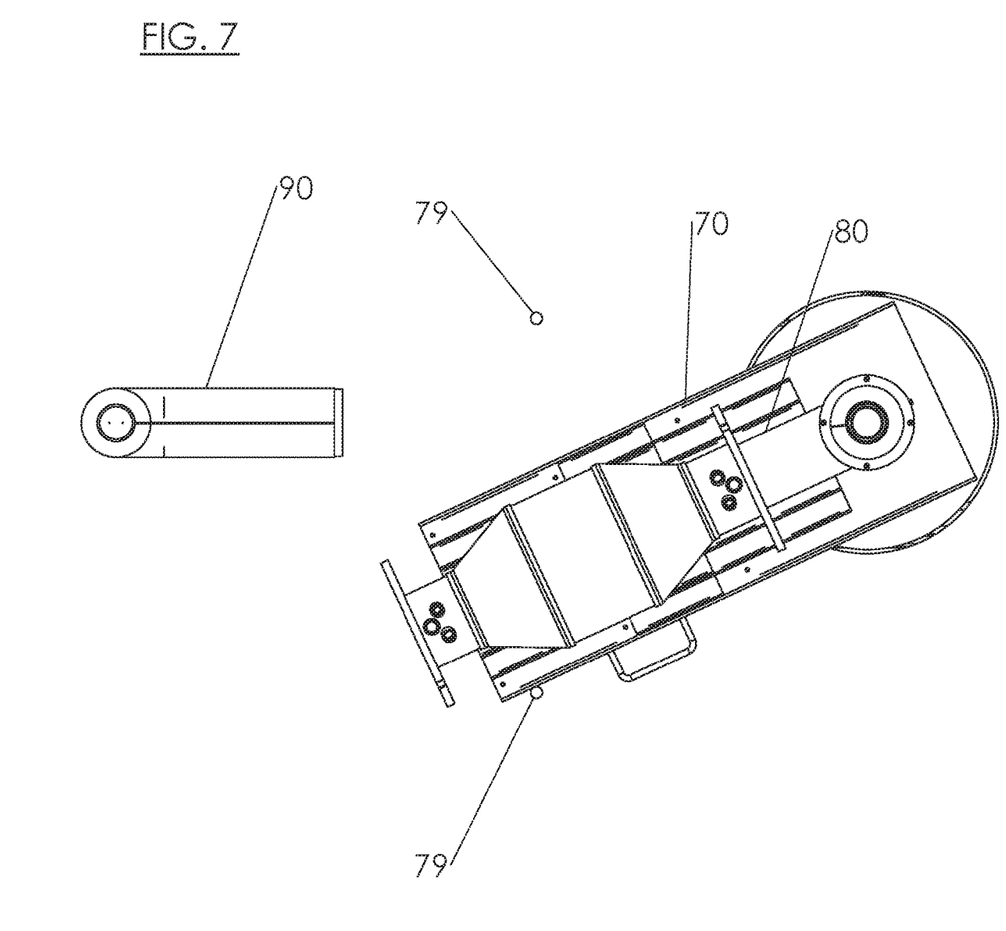
FIG. 7 is a top view of the system of FIG. 6. The pivot table moves through an arc between an unaligned (load) position, shown here, and an aligned (pre-test) position as shown in FIGS. 6 & 8. Although not preferred, depending on the size and weight of the element housing, table could be arranged to work in a vertical position.
Figure 8:
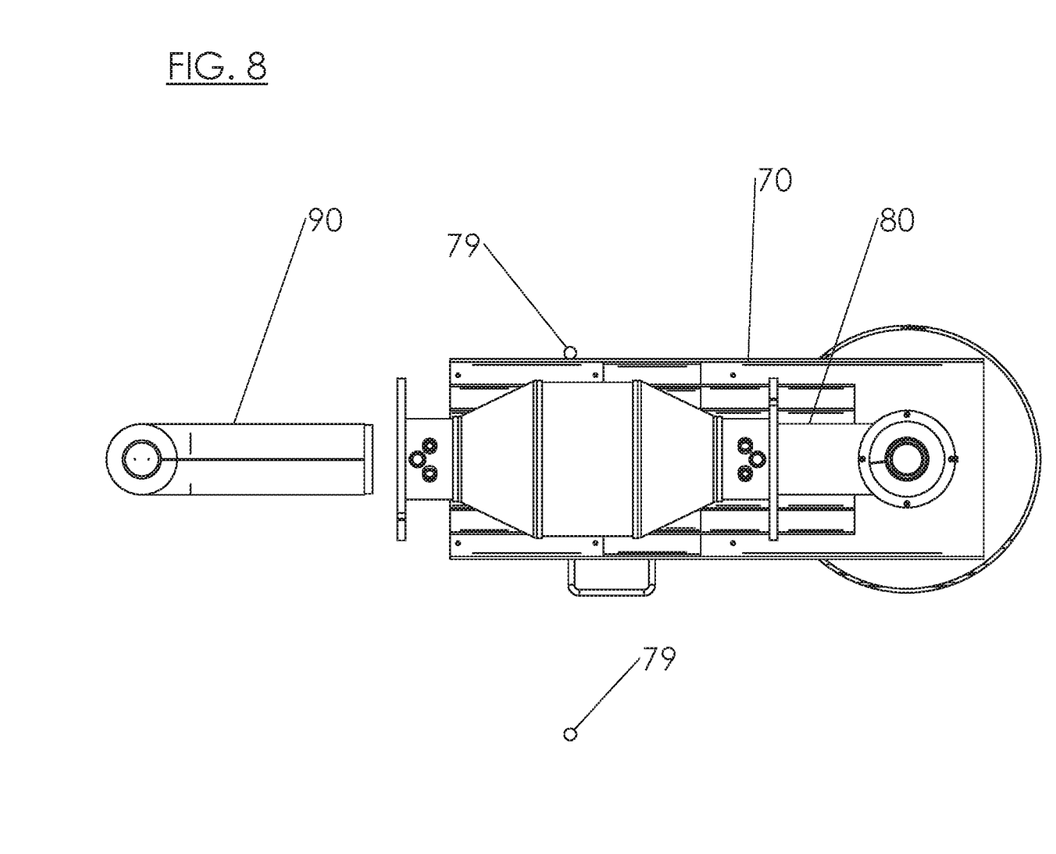
FIG. 8 is a top view of the system of FIG. 6 with the pivot table in the aligned or pre-test position. The catalyst inlet and outlet pipes move axially into a sealing position with an opposing face surface of the catalyst element.

Pivot table 70 moves through an arc between a load position, in which the sealing ends 83, 93 of the adaptor 80 and catalyst outlet pipe 90 are not aligned, and a pre-test position, in which the sealing ends 83, 93 are aligned with one another. Stops 79 define the load and pre-test positions and limit the table's 70 range of motion. In the load position, slides 77 move inward or outward of the centerline of the table 70 to adjust its width to receive and temporally secure different sized catalyst housings.

Figure 9:
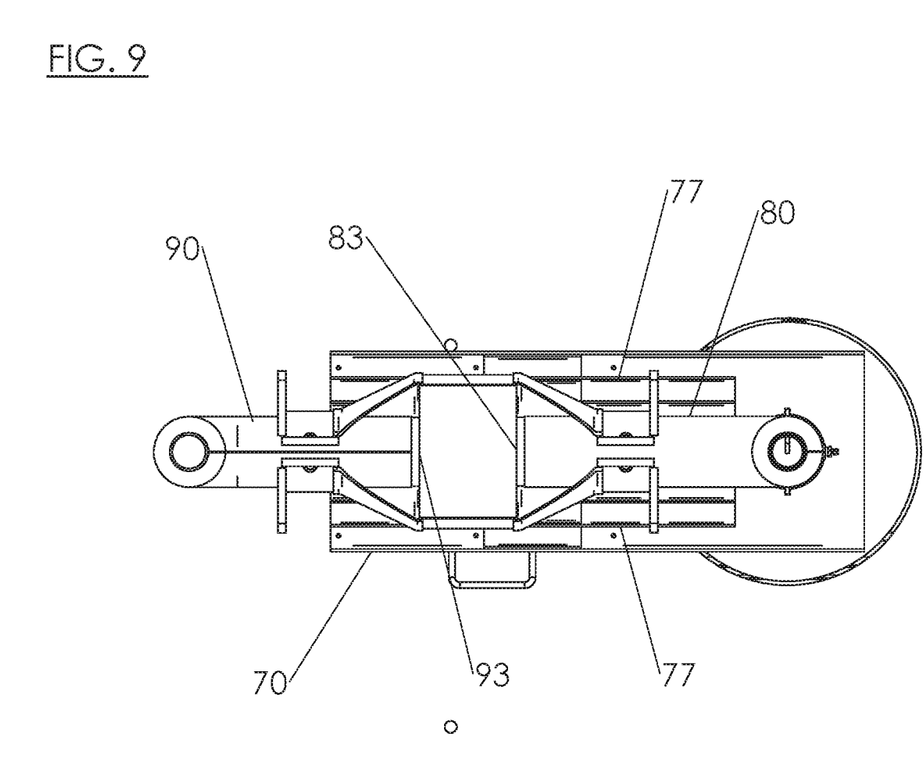
FIG. 9 is a top view of the system of FIG. 6 with the catalyst inlet and outlet pipes in a sealing or test position.
Figure 10:
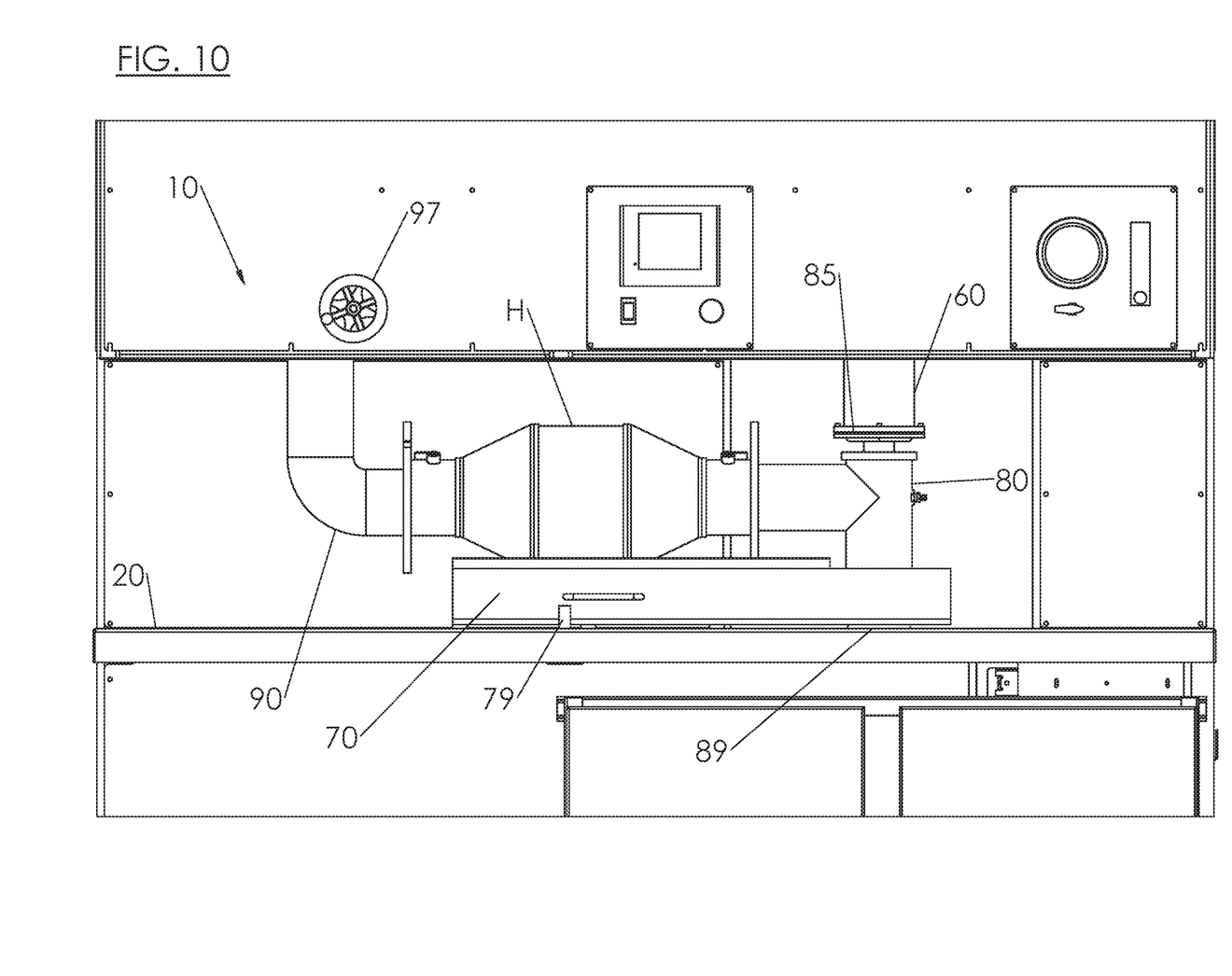
FIG. 10 is a side view of the system of FIG. 6 with the catalyst inlet and outlet pipes in the sealing or test position.

Once table 70 is in the pre-test position, a screw jack 87 or its equivalent is used to move at least one of the ends 83, 93 of the catalyst inlet pipe adaptor 80 and outlet pipe 90 into a test position, that is, toward one another and into sealing engagement with an opposing face surface of the catalyst element. Preferably, as the element housing H is loaded onto table 70, the face surface of the catalyst element placed into contact with end 83 of the catalyst inlet pipe adaptor, with the screw jack 87 moving the outlet pipe 90 axially so its end 83 contacts the opposing face surface of the catalyst element.

Figure 6:
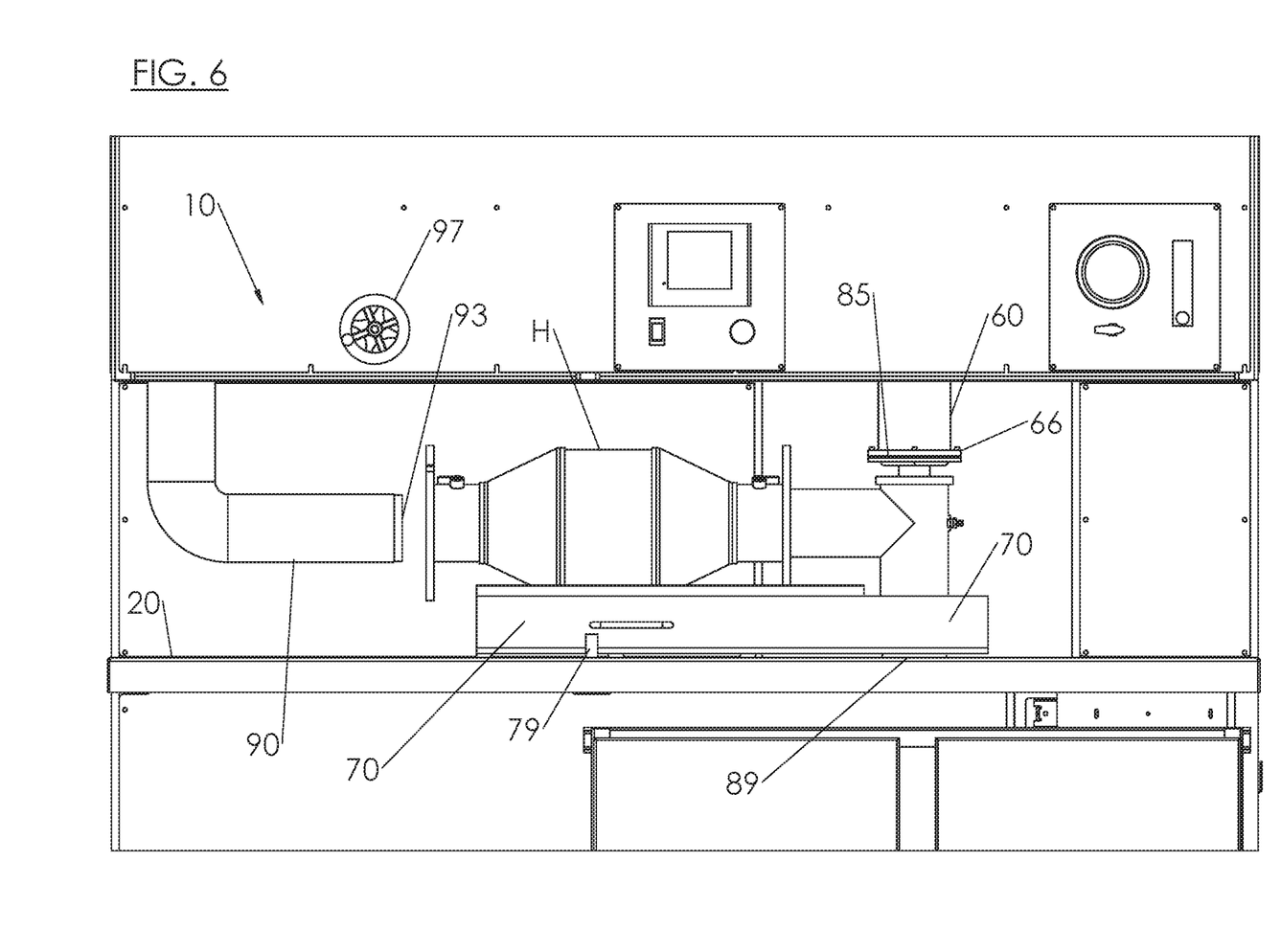
FIG. 6 is a side view of an alternate embodiment of the test stand which practices the system and method of this invention. A pivot table with a catalyst inlet piping is placed above the stand's table top and permits testing of a completely enclosed or in-situ (housed) catalyst element like that used in industrial engines. The stand is shown in its aligned or pre-test position.

Catalyst inlet pipe adapter 80 connects to inlet pipe 20, with the pivot table 70 having a larger opening 74 about the adaptor 80 to create a circumferential gap about the lower end 89 of the adaptor 73 (similar to that of opening 54 about inlet pipe 20 as shown in FIG. 5). The upper end 87 of the adaptor 80 seals against and blocks the lower end 66 of the catalyst outlet pipe 60. Additional heating elements (not shown) can be placed on the catalyst inlet pipe adaptor 80 if desired.

Although preferred embodiments of a test system and method have been disclosed, changes can be made in its construction or arrangement of parts and steps. Therefore, the scope of the invention is limited only by the following claims and equivalent elements thereof.

What is claimed:
1. A non-destructive testing system comprising:
a surface including a catalyst inlet piping opening;
a catalyst inlet piping and a catalyst outlet piping each arranged on opposing sides of the surface;
sealing means located at an opposing facing end of the catalyst inlet and outlet pipings, respectively; the sealing means configured to seal against an inlet and outlet face of a portion of a catalyst element when resting on the surface and the opposing facing ends are in contact with the inlet and outlet faces of the portion; and
means to change the relative linear distance between the opposing facing ends.
2. A system according to claim 1 further comprising a pivot table arranged to move the catalyst inlet piping into alignment with the opening of the surface.
3. A system according to claim 1 further comprising a source of a main fluid stream and a source of a test fluid stream, the catalyst inlet piping being in communication with the main fluid and test fluid sources.
4. A system according to claim 3 further comprising the source of the test fluid stream including propane.
5. A system according to claim 3 further comprising a heater located between the source of the main fluid stream and the catalyst inlet piping.
6. A system according to claim 5 further comprising means for the test fluid stream to bypass the heater.
7. A system according to claim 3 further comprising a mixer arranged to mix the main fluid stream and the test fluid stream with one another.
8. A system according to claim 1 further comprising the catalyst inlet piping opening of the surface being larger in diameter than that of the catalyst inlet piping.

9. A system according to claim 1 further comprising at least one of the catalyst inlet and outlet pipings having a port through which a fluid passing through the piping may be sampled.

10. A system according to claim 1 wherein the surface is a flat surface.

11. A system according to claim 1 wherein the surface is arranged in a horizontal plane.

12. A system according to claim 1 wherein the surface is arranged in a vertical plane.

13. A system according to claim 1 wherein the surface is a flange.

14. A non-destructive testing system according to claim 1 wherein said catalyst inlet piping opening is larger in diameter than said catalyst inlet pipe for providing a circumferential gap between said surface and said catalyst inlet piping.

15. A non-destructive testing system according to claim 1 wherein said means to change is a screw jack.

16. A method for non-destructive testing, the method comprising:
   (i) sealing a catalyst inlet pipe and a catalyst outlet pipe located on opposite sides of a monolith catalyst element against an inlet face and outlet face surface, respectively, of a portion of the monolith catalyst element, and
   (iii) passing a test fluid stream between the catalyst inlet and outlet pipes and through the sealed portion of the monolith catalyst element;
wherein the passing step system allows activity of the sealed portion of the monolith catalyst element to be tested without removing it from the monolith catalyst element.

17. A method according to claim 16 further comprising moving at least one of the catalyst inlet and outlet pipes toward one another prior to sealing.

18. A method according to claim 16 further comprising aligning the catalyst inlet and outlet pipes with one another prior to sealing.

19. A method according to claim 18 wherein the aligning moves the at least one of the catalyst inlet and outlet pipes through an arc.

20. A method according to claim 18 wherein the aligning occurs in a horizontal plane.

21. A method according to claim 16 further comprising mixing a main fluid stream with the test fluid stream, the mixing step occurring before the passing step.

22. A method according to claim 21 further comprising heating the main fluid stream, the heating step occurring before the mixing step.

23. A method according to claim 16 further comprising locating said monolith catalyst element on a surface defining an opening, wherein said opening is larger than at least one of said catalyst inlet pipe and said catalyst outlet pipe for providing a circumferential gap between said surface and said catalyst inlet piping.

24. A method according to claim 16 wherein said step of sealing comprises changing the relative distance between said inlet face and said outlet face.

25. A method according to claim 24 wherein said step of changing the relative distance utilizes a screw jack.

26. A non-destructive testing system comprising:
   a surface including an opening;
   a test fluid inlet piping located on one side of the opening;
   a test fluid outlet piping arranged on an opposing side of the opening;
   the pipings each including a seal on a surface-facing end;
   means to change the relative linear distance between at least one of the pipings and the surface;
   wherein when in use the seals seal against a portion of a catalyst element resting on the surface between the pipings and blocking the opening.

27. A non-destructive testing system according to claim 26, further comprising the opening being larger in diameter than at least one of the pipings.

* * * * *